United States Patent [19]
Mygind et al.

[11] 4,385,048
[45] May 24, 1983

[54] METHODS FOR THE TREATMENT OF NASAL HYPERSECRETION

[75] Inventors: Niels Mygind, Birkeroed; Peter Borum, Soeborg, both of Denmark; Christiane Grieben, Ingelheim am Rhein, Fed. Rep. of Germany

[73] Assignee: Boehringer Ingelheim GmbH, Ingelheim am Rhein, Fed. Rep. of Germany

[21] Appl. No.: 208,411

[22] Filed: Nov. 14, 1980

Related U.S. Application Data

[63] Continuation-in-part of Ser. No. 24,118, Mar. 26, 1979, abandoned.

[30] Foreign Application Priority Data

Feb. 2, 1979 [DE] Fed. Rep. of Germany ....... 2903957

[51] Int. Cl.³ ............................................. A61K 31/435
[52] U.S. Cl. ...................................... 424/45; 424/256
[58] Field of Search .................................. 424/45, 256

[56] References Cited

U.S. PATENT DOCUMENTS 3,312,709 4/1967 MacMillan ............................ 546/91
3,472,861 10/1969 Zeile et al. ............................ 546/91

FOREIGN PATENT DOCUMENTS 555763 4/1958 Canada .

OTHER PUBLICATIONS

Goodman & Gilman, "The Pharmacological Basis of Therapeutics", 6th Ed., (1980), pp. 134–135.
Chemical Abstracts, (Deckers), 84:173577f, (1976).
Goodman & Gilman–"The Pharmacological Basis of Therapeutics", 3rd Ed., 1965, pp. 521–527, & 540.
Chemical Abstracts, 84:44483y, (1976).

Primary Examiner—Leonard Schenkman
Attorney, Agent, or Firm—Hammond & Littell, Weissenberger & Muserlian

[57] ABSTRACT

Compositions for the treatment of nasal hypersecretion comprising (8r)-8-isopropyl-3α-[(±)-tropoyl-oxy]-1αH, 5αH-tropanium bromide in a pharmaceutical formulation suitable for topical application to the nasal cavity; and methods of use.

6 Claims, No Drawings

METHODS FOR THE TREATMENT OF NASAL HYPERSECRETION

This is a continuation-in-part of copending application Ser. No. 024,118, filed Mar. 26, 1979, now abandoned.

This invention relates to novel compositions for the treatment of nasal hypersecretion and methods of use.

BACKGROUND OF THE INVENTION

For the treatment of nasal hypersecretion (commonly referred to as "runny nose") various groups of active substances are presently used, but the results are in no case completely satisfactory. For example, it is known to use vasoconstrictors with aminoethanol or imidazoline structures, but side-effects such as strong dryness-of-the-mouth as well as possibly also systemic effects and the so-called rebound-phenomenon have to be accepted. Furthermore, disodium cromoglycate (DSCG) or corticosteroids such as beclomethasone dipropionate are in use. However, these active substances mainly relieve the symptoms of the allergenic variants of perennial rhinitis, for instance the so-called hay fever; moreover, in connection with the use of corticosteroids (especially in the case of long-term treatment) the special risks of this class of substances (occurrence of mycoses, negative effect on the mineral balance and blood sugar level, mucous membrane atrophy) have to be taken into account.

OBJECTS OF THE INVENTION

It is an object of this invention to provide compositions which make possible a practically side-effect-free therapy of all manifest forms of nasal hypersecretion.

Other objects and advantages of the invention will become apparent as the description thereof proceeds.

DESCRIPTION OF THE INVENTION

We have discovered that the above object is achieved by topical administration of a quaternary tropane alkaloid derivative which exhibits an atropine-like, i.e. vagus-blocking, activity in the area of the nasal mucous membrane. The compositions according to the present invention, therefore, are pharmaceutical preparations of a tropane alkaloid derivative suitable for topical administration to the nasal mucous membrane with a specific vagus-blocking effect at the point of application.

The active ingredient of the compositions according to the present invention is (8r)-8-isopropyl-3α-[(±)-tropoyl-oxy]-1αH, 5αH-tropanium bromide, also known as N-isopropyl nortropine tropic acid ester methobromide or by its generic name ipratropium bromide, for the formula

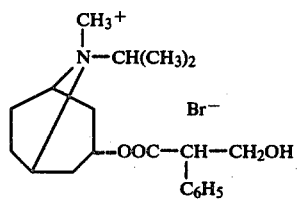

Formulations of this active substance suitable for topical application to the nasal mucous membrane are, for example, aqueous solutions (applicable by way of nose-dropper) or—preferably—aerosols, where those operated by means of propellant gases or also propellant gas-free aerosols, such as the so-called metering pump aerosols, may be used. The latter are generally preferred because of their low irritating effect on the nasal mucous membrane.

The novel compositions according to the invention provide for the first time the possibility of rapidly and surely bringing also non-allergenic forms of perennial rhinitis under control without the occurrence of undesirable side-effects. They further make it possible to combat nasal hypersecretion already in the initial stage. The daily dose amounts to between 150–500 mcg, preferably 200–350 mcg. In the case of a metered aerosol which delivers, for example, 20 mcg of active ingredient per actuation, two or possibly three actuations with a single dose of 40–60 mcg are sprayed three to four times daily into each nostril, so that a total daily dose between 240 and 480 mcg is achieved.

It is also possible to combine the tropane alkaloid derivative according to the invention with other active ingredients which are active in the nose, such as beclomethasone dipropionate or fenoterol. Especially the combination with fenoterol produces very favorable effects, because it is thereby possible also to include allergenic forms of rhinitis in the treatment. In this combination the daily dose of fenoterol can be up to 4 times higher than the daily dose of ipratropium bromide, which is due to the different activities of the two substances.

The following examples illustrate the present invention and will enable others skilled in the art to understand it more completely. It should be understood, however, that the invention is not limited solely to the particular examples given below. The parts are parts by weight unless otherwise specified.

EXAMPLE 1

Metering Pump Aerosol

The aerosol composition is compounded from the following ingredients:

| | |
|---|---|
| Ipratropium bromide | 3.33 mgm |
| Surfactive substance, for instance benzalkonium chloride | 5.00 mgm |
| 1N HCl (for adjustment of the pH to 3.4) | 0.018 ml |
| Demineralized water ad | 20 ml |

The ingredients are dissolved in the demineralized water, and the solution is filled into a bottle provided with a metering pump aerosol device which is additionally equipped with a nose adapter. The pump of the aerosol is adjusted so that it expels 60 μl of the solution per stroke.

In place of 3.33 mgm active substance, an amount of 16.67 mgm active substance may also be used. In this manner an aerosol liquid with a higher dose is obtained for the purpose of treating stubborn cases.

EXAMPLE 2

Metered-dose aerosol with propellant gas

The aerosol composition is compounded from the following ingredients:

| | |
|---|---|
| Ipratropium bromide | 0.02 parts |
| Surfactive substances, for instance sorbitan trioleate | 0.03–0.3 parts |

| | |
|---|---|
| Propellant gas mixture of monofluoro-trichloromethane, difluoro-dichloromethane and tetrafluoro-dichloromethane   ad | 70 parts |

The ingredients are admixed with each other in conventional manner, and an amount of the mixture corresponding to about 200 single doses is filled into an aerosol can equipped with a metering valve and a nose adapter.

EXAMPLE 3

Nose Drops

The drop solution is compounded from the following ingredients:

| | | |
|---|---|---|
| Ipratropium bromide | | 0.25 parts |
| Fenoterol | | 1.00 parts |
| Demineralized water | ad | 10,000 parts by vol. |

The active ingredients are dissolved in the demineralized water, and the solution is filled into small brown bottles which are closed with a threaded cap comprising a built-in nose dropper. The doses of the active ingredients are such that, by means of 2 to 3 drops (0.1 to 0.15 ml), the suitable single dose of the tropane alkaloid (about 20 to 25 mcg for each nostril) can be applied to the nasal mucous membrane.

The amount of active ingredient in illustrative Examples 1–3 may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of treating nasal hypersecretion, which comprises topically administering to the nasal mucous membrane an effective nasal hypersecretion inhibiting amount of a topical pharmaceutical composition consisting essentially of an inert liquid carrier suitable for topical administration to the nasal mucous membrane and an effective nasal hypersecretion inhibiting amount of N-isopropyl-nortropine tropic acid ester methobromide.

2. The method of claim 1, where said inert liquid carrier is water.

3. The method of claim 1, where said inert liquid carrier is an acidic aqueous solution of a surfactant.

4. The method of claim 1, where said inert liquid carrier is a propellant gas mixture of monofluoro-trichloromethane, difluoro-dichloromethane and tetrafluoro-dichloromethane comprising a surfactant.

5. The method of claim 1, where said composition additionally comprises an effective amount of another nasally active ingredient.

6. The method of claim 5, where said other nasally active ingredient is fenoterol.

* * * * *